(12) United States Patent
Olbrich et al.

(10) Patent No.: US 6,733,464 B2
(45) Date of Patent: May 11, 2004

(54) MULTI-FUNCTION SENSOR DEVICE AND METHODS FOR ITS USE

(75) Inventors: Craig A Olbrich, Corvallis, OR (US); John Stephen Dunfield, Corvallis, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 0 days.

(21) Appl. No.: 10/226,597

(22) Filed: Aug. 23, 2002

(65) Prior Publication Data
US 2004/0039295 A1 Feb. 26, 2004

(51) Int. Cl.[7] .................................................. A61B 5/08
(52) U.S. Cl. ......................................................... 600/538
(58) Field of Search ................................. 600/538, 537, 600/533, 532, 529, 531

(56) References Cited

U.S. PATENT DOCUMENTS

| | | | |
|---|---|---|---|
| 4,407,295 A | 10/1983 | Steuer et al. | |
| 4,736,750 A | 4/1988 | Valdespino et al. | |
| 4,830,022 A | * 5/1989 | Harshe et al. | ............... 600/537 |
| 5,137,026 A | 8/1992 | Waterson et al. | |
| 5,179,958 A | 1/1993 | Mault | |
| 5,277,195 A | 1/1994 | Williams | |
| 5,518,002 A | 5/1996 | Wolf et al. | |
| 5,562,101 A | 10/1996 | Hankinston et al. | |
| 5,642,735 A | 7/1997 | Kolbly | |
| 5,827,179 A | 10/1998 | Lichter et al. | |
| 5,894,841 A | 4/1999 | Voges | |
| 6,004,277 A | 12/1999 | Maharaj et al. | |
| 6,019,731 A | 2/2000 | Harbrecht et al. | |
| 6,030,350 A | * 2/2000 | Jiang et al. | ................. 600/587 |
| 6,159,147 A | 12/2000 | Lichter et al. | |
| 6,165,155 A | 12/2000 | Jacobsen et al. | |
| 6,183,423 B1 | * 2/2001 | Gaumond et al. | .......... 600/529 |
| 6,190,326 B1 | 2/2001 | McKinnon et al. | |
| 6,196,218 B1 | 3/2001 | Voges | |
| 6,238,352 B1 | 5/2001 | Gillings et al. | |

FOREIGN PATENT DOCUMENTS

WO      WO/90/04945      5/1990

* cited by examiner

*Primary Examiner*—Max F. Hindenburg
*Assistant Examiner*—Navin Natnithithadha (57) ABSTRACT

A portable sensor device for obtaining physiological information, including cardiopulmonary information, from a human or animal subject. The device includes a housing having a lumen and a respiratory port in fluid communication with the lumen. The lumen can be divided into plural airflow tubes. Spirometric data can be integrated with non-spirometric cardiopulmonary data collected by the device. Additionally, the sensor device can be operably coupled to a bioactive composition delivery device. Methods for using the sensor device and methods for making the sensor device also are disclosed.

53 Claims, 4 Drawing Sheets

MULTI-FUNCTION SENSOR DEVICE AND METHODS FOR ITS USE

FIELD

This invention relates to medical devices for sensing and measuring biological activity. More particularly, this invention relates to portable bio-sensors, including self-contained bio-sensors, capable of sensing and measuring cardiopulmonary activity.

BACKGROUND

A large number of chronic diseases are related to the dysfunction of the cardiopulmonary system. Modern lifestyles and environments predispose individuals to chronic obstructive pulmonary disorders (such as asthma and chronic obstructive pulmonary disease) and ischemic heart disease. Moreover, the cardiopulmonary system is functionally interconnected in many respects, such that alterations in heart function are sometimes associated with changes in the lungs.

The prevalence of heart and lung disorders has led to the development of many devices for detecting and monitoring dysfunction in these organ systems. An example of such a device is the spirometer, which is an instrument for collecting data about breathing capacity and other pulmonary functions. Spirometers are utilized for diagnosis of lung diseases and conditions, such as asthma, chronic bronchitis, emphysema, and other chronic obstructive pulmonary disorders (COPD); black lung disease, asbestosis, and other occupational lung diseases; and cystic fibrosis and other congenital diseases.

Spirometers are often large, bulky devices located in a hospital, doctor's office, or other clinical setting. In recent years, however, some portable spirometers have been designed and manufactured. These previously known portable spirometers share a similar design based around a single tube having a mouthpiece and an exhaust port. A person using a portable spirometer blows air into the mouthpiece, through the tube (where the airflow is measured by one or more sensors), and out the exhaust port. Raw data collected by the spirometer can be used to determine various spirometric parameters in a Pulmonary Function Test (PFT), such as vital capacity (VC), which is the maximum volume of air that can be expired slowly after a full inspiratory effort; forced vital capacity (FVC), which measures the volume of air expelled from the lungs with maximal force; tidal volume (TV), which measures the volume of air inspired or expired with each breath; total lung capacity (TLC), which is the total volume of air within the chest after a maximum inspiration; peak expiratory flow (PEF), which is a measure of the highest airflow rate from the lungs during forced exhalation; maximal voluntary ventilation (MVV), which is the volume of air expired during breathing at the maximal TV and respiratory rate for twelve seconds; and forced expired volume during the first second ($FEV_1$), which is the volume of air forcibly expelled in one second of time. Other PFTs are disclosed in Beers, M. H. and Berkow, R. (eds), The Merck Manual of Diagnosis and Therapy (Merck Research Laboratories, Whitehouse Station, N.J., 1999), chapter 64.

Previously known spirometers, including portable spirometers, do have some limitations, however. For example, some spirometers can measure only a single parameter (such as only PEF), while other spirometers have a single tube of a fixed diameter and can accurately measure only airflow rates within a certain range. Moreover, most spirometers are limited to collecting only spirometric data and not any other potentially useful physiological data.

SUMMARY

Disclosed is a sensor device for obtaining cardiopulmonary data from a subject. The sensor device includes an elongated housing having a proximal end, a distal end, and a lumen. The lumen can be divided into one or more airflow tubes. The proximal housing end defines a respiratory port that is in fluid communication with the lumen, and an airflow port is defined in the housing adjacent the distal end of the lumen. The airflow port also is in fluid communication with the lumen.

An airflow sensor is positioned within the lumen and is capable of measuring pulmonary airflow through the lumen as the subject exhales or inhales. Also positioned within the lumen is a non-spirometric cardiopulmonary activity sensor. A data processor is operably coupled to both the airflow sensor and the non-spirometric cardiopulmonary activity sensor. Thus, the sensor device is capable of integrated collection of cardiopulmonary data obtained via the airflow sensor and the non-spirometric cardiopulmonary activity sensor.

DETAILED DESCRIPTION

The singular forms "a," "an," and "the" refer to one or more than one, unless the context clearly dictates otherwise. For example, the term "comprising a tube" includes single or plural tubes and is considered equivalent to the phrase "comprising at least one tube."

The term "or" refers to a single element of stated alternative elements or a combination of two or more elements. For example, the phrase "obtaining measurements from a first sensor or a second sensor" refers to obtaining measurements from the first sensor, obtaining measurements from the second sensor, or obtaining measurements from both the first and second sensors.

The term "comprises" means "includes." Thus, "comprising an airflow sensor and a temperature sensor" means "including the airflow sensor and temperature sensor," without excluding additional elements.

The term "subject" includes both human and non-human (veterinary) subjects, for example, non-human primates, dogs, cats, horses, sheep, birds, and reptiles. In particular embodiments, the subject is a human.

Spirometry is the measurement of air during inhalation and/or exhalation, and includes measurement using a Pulmonary Function Test (PFT). Exemplary, non-limiting PFTs are described herein, including vital capacity (VC), forced vital capacity (FVC), tidal volume (TV), total lung capacity (TLC), peak expiratory flow (PEF), maximal voluntary ventilation (MVV), and forced expired volume during the first second ($FEV_1$). As used herein, the term "spirometry" is intended to encompass the general meaning of the word and any other pulmonary function that can be detected by measuring air pressure, volume, flow, air temperature, or a combination thereof.

Disclosed is a sensor device for obtaining physiological information from a subject, such as information about body temperature and cardiopulmonary function, including (but not limited to) lung capacity, airflow during inhalation or exhalation, respiration rate, lung or bronchial abnormalities, heart rate, blood oxygen concentration, and heartbeat. Some embodiments of the device allow simultaneous or near-simultaneous measurement of lung function, body temperature, and some other cardiopulmonary parameter, such as heart rate or heart rhythm.

In some embodiments, the sensor device is a spirometric measurement device that includes an additional sensor for gathering body temperature, such as a digital thermometer. In other embodiments, the device includes a sensor for gathering spirometric data and a sensor for measuring non-spirometric cardiopulmonary information, such as an oximeter for measuring blood oxygen concentration, and/or a sensor for sensing cardiac and/or respiratory sounds (such as a microphone), and/or a sensor for monitoring electrical activity of the heart (such as an electrocardiograph).

Some embodiments of the sensor device utilize a single airflow tube for gathering spirometric data. Alternative embodiments utilize plural airflow tubes, such as airflow tubes of different diameters, for redundant measurement of airflow. During inhalation or exhalation, the subject forces air into an airflow tube defined within the device, and an airflow sensor within the tube measures the airflow. In embodiments having plural airflow tubes, airflow data can be collected from a sensor within a single tube or from an array of plural sensors within plural tubes.

Data collected by the various sensors within the device can be integrated, correlated, and stored within the sensor device for later retrieval. For example, airflow measurements can be correlated with body temperature and/or some non-spirometric cardiopulmonary attribute, such as heart rate, and this integrated information can be later transferred to a computer. Alternatively, raw (unintegrated) data collected by the device can be stored for later retrieval or transferred to an external repository without first being stored within the device.

Methods for using this sensor device include collecting information about the cardiopulmonary status of a subject for the diagnosis and/or prognosis of physiological disease or disorders, such as pulmonary disorders including (but not limited to) asthma, chronic bronchitis, emphysema, and other chronic obstructive airway disorders (COPD); pneumonia and other infectious diseases; asbestosis and other occupational lung diseases; pulmonary embolus; idiopathic interstitial lung diseases, such as idiopathic pulmonary fibrosis; pleural disorders; tumors of the lung; allergies; and other respiratory problems. Other methods for using the device include remote monitoring of a subject having a cardiopulmonary disease or disorder, assessing a subject's physiological response to a particular medication or treatment regimen via biofeedback, and gathering baseline data for later comparison. A method of manufacturing the device also is disclosed.

Figure 1:
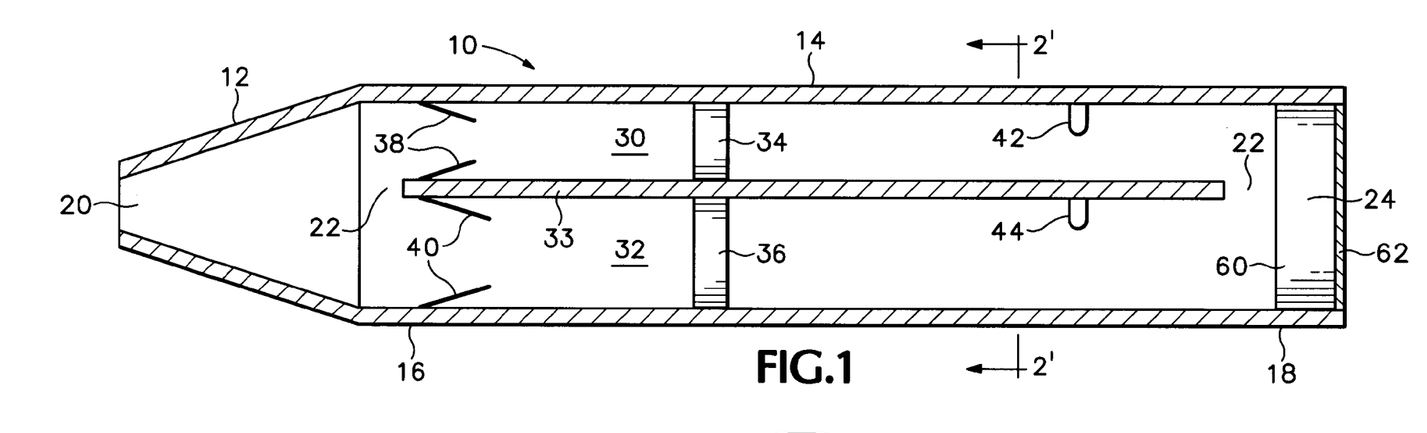
FIG. 1 illustrates a longitudinal section through one embodiment of the sensor device.
Figure 2:
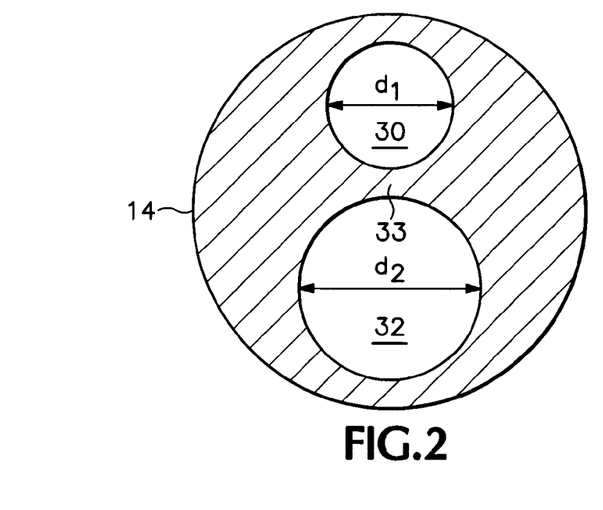
FIG. 2 illustrates a cross-sectional view through line 2'–2' of the embodiment illustrated in FIG. 1.

FIGS. 1–2 show one embodiment of the sensor device. In FIG. 1, device 10 includes mouthpiece 12 and elongated housing 14, which has a proximal end 16 and a distal end 18. Mouthpiece 12 defines a respiratory port 20 in fluid communication with housing lumen 22, while distal end 18 of housing 14 includes airflow port 24 also in fluid communication with housing lumen 22.

Mouthpiece 12 can be dimensioned for use by any appropriate subject, such as being dimensioned to fit the mouth of a human adult or child. In some embodiments, however, mouthpiece 12 is dimensioned to fit the mouth of a young or adult non-human animal, such as a horse, dog, cat, or other domesticated animal.

In alternative embodiments, mouthpiece 12 is dimensioned for insertion into a nostril of the subject, or into both nostrils of the subject at the same time. Therefore, the term "mouthpiece" should not be interpreted as limiting the use of the device within the mouth of a subject. For example, an embodiment having a mouthpiece 12 sized for insertion into a nostril can be used to detect airflow through the nostrils and sinus cavities. Alternatively, an embodiment having a microphone and recording device (for example, a microphone in operable connection to a digital recording device), as described herein, can be used to record sounds of airflow through the sinuses and nasal passages. A user of the device, such as the subject or a health care professional, also can tap on the subject's head adjacent the nasal passages and the device can detect (and record) the sounds transmitted through the sinuses and nasal cavities. Detecting and/or recording sounds in this manner can assist in determining various sinus conditions, such as a sinus infection or physical obstruction of the sinuses.

When using the device, the subject exhales or inhales through respiratory port 20 of mouthpiece 12, which forces air through housing lumen 22 from airflow port 24 (if the subject inhales) or out through airflow port 24 (if the subject exhales). In particular embodiments, the subject exhales through respiratory port 20 of mouthpiece 12 forcing air through housing lumen 22 and out through airflow port 24. In such embodiments, airflow port 24 functions as an exhaust port.

Mouthpiece 12 can be formed from the same piece of material as housing 14 to provide a unibody construction. However, in some embodiments, mouthpiece 12 is a separate piece removably coupled to housing 14. For example, the mouthpiece and housing can be coupled together by a set of screw threads or clips, or the wider part of the mouthpiece can be sized to snugly fit over the proximal end of the housing. Additionally, both housing 14 and mouthpiece 12 can be constructed from multiple pieces of material.

Mouthpiece 12 and housing 14 can be formed from any suitable substantially air-impermeable material—such as metal, alloys, plastic or other polymers, ceramics, cardboard, or composite materials—that provides suitable strength during use. Particular embodiments utilize a mouthpiece and housing constructed from polymer or composite materials, such as plastic, that provide sufficient strength while reducing the weight of the device compared to other materials, such as metals and alloys. Other particular embodiments of the device utilize medically acceptable plastics and/or metals in their construction.

While FIGS. 1 and 2 illustrate a cylindrical device having a circular cross-section, alternative embodiments employ devices of different shapes, such as devices have square, oval, triangular, hexagonal, octoganal, or other shaped cross-sections. Additionally, an airflow tube can be the same shape as the housing or a different shape. As just one example, a columnar housing (having a square cross-section) can include a cylindrical airflow tube (having a circular cross-section).

Device 10 can be any appropriate size and can be sized for use with particular subjects. For example, portable devices for human use can be from about 5 to about 25 cm in length with an overall diameter of from about 5 mm to about 6 cm. Particular embodiments intended for human use utilize a device that is from about 8 to about 15 cm long with an overall diameter of from about 1 cm to about 3 cm. Other embodiments can be sized appropriately. For example, embodiments intended for use with large animals, such as horses, can have larger dimensions, while embodiments intended for use with smaller animals, such as certain breeds of domesticated cats and dogs, can have smaller dimensions.

Figure 3:
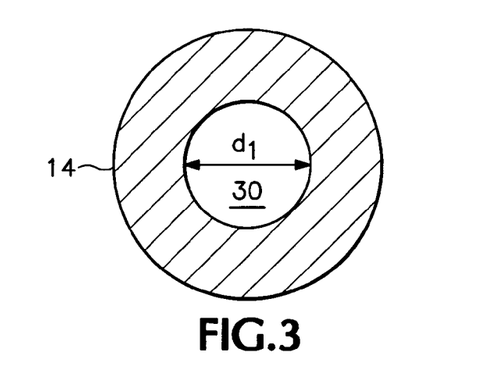
FIG. 3 illustrates a cross-sectional view of an alternative embodiment having a single airflow tube. This view is similar to the cross-sectional view illustrated in FIG. 2.

In the embodiment illustrated in FIG. 1, housing lumen 22 is divided into first airflow tube 30 and second airflow tube 32 by interior wall 33. Alternative embodiments utilize a single airflow tube or more than two airflow tubes, such as three, four, five, six, or more airflow tubes. For example, FIG. 3 illustrates an alternative embodiment having only a first airflow tube 30, which structurally is housing lumen 22.

The diameters of the airflow tubes can be any appropriate size, such as a diameter from about 1 mm to about 2 cm, from about 2 mm to about 1.5 cm, or from about 2 mm to about 1 cm. The diameters of plural airflow tubes can be identical, substantially similar, or substantially different. In particular embodiments, each of two or more airflow tubes has a substantially different diameter. For example, as illustrated in FIG. 2, the diameter ($d_1$) of first airflow tube 30 is substantially less than the diameter ($d_2$) of second airflow tube 32. In one exemplary embodiment (and without limitation), $d_1$ is 2.5 mm, while $d_2$ is 5.0 mm.

In the illustrated embodiment, the airflow tubes extend linearly along the longitudinal axis of the housing. In other embodiments, however, the airflow tubes do not extend in a linear manner, or are otherwise oriented in a direction that does not lie substantially parallel to longitudinal axis of the housing. For example, some embodiments utilize curving airflow tubes, such as S-shaped or U-shaped airflow tubes, displaced within the housing. In other exemplary embodiments, the housing contains a plurality of linear airflow tubes extending substantially perpendicular to the longitudinal axis of the housing, similar to the arrangement of chambers in a harmonica.

While the device can utilize only a single airflow tube, devices utilizing plural airflow tubes have the additional feature of allowing redundant airflow measurements or directing airflow to an appropriately sized airflow tube. For example and referring to the embodiment illustrated in FIGS. 1 and 2, a person can hold mouthpiece 12 between the lips and blow through respiratory port 20. The forced air would enter housing lumen 22, then enter the first airflow tube 30 and second airflow tube 32, then pass along or through first airflow sensor 34 and second airflow sensor 36. Depending on the force of the expired breath and the range of accuracy of the airflow sensors, airflow measurements can be taken in either airflow tube or both tubes.

In the illustrated embodiment, first airflow tube 30 contains first gate 38 and second airflow tube 32 contains second gate 40. These gates 38, 40 can block airflow into tubes 30, 32 by shutting. Thus, airflow can be directed into one of the tubes, both tubes, or neither tube. Airflow can be directed using mechanisms other than gates, however. For example, the illustrated gates can be replaced by irises, slidable doors, individual drop-down doors, or other airflow director. Alternatively, a single moveable gate or door can be placed at the proximal end of interior wall 33 for shunting air into either tube or, if left in a middle position, to allow airflow through both tubes. In other embodiments, however, the device does not include an airflow director.

Gates 38, 40 (or an alternative airflow director) can be placed in any appropriate position within tubes 30, 32 or lumen 22, so long as they are capable of blocking airflow to or directing airflow away from airflow sensors 34, 36. For example, device 10 illustrated in FIG. 1 is intended for use in detecting and measuring airflow during exhalation. The direction of airflow is from proximal mouthpiece 12 to distal airflow port 24. An alternative embodiment has an additional set of gates (or a single set of gates) within tubes 30, 32 distal of temperature sensors 42, 44 capable of blocking airflow entering through distal airflow port 24 during inhalation.

The airflow director facilitates directional airflow through the device. For example, certain embodiments are designed to measure unidirectional airflow (either inhalation or exhalation), and the gates (or their alternatives) can block airflow not conforming to the intended direction. Additionally, the airflow director assists in controlling airflow through particular tubes within a device. For example, in the illustrated embodiment, airflow through tubes 30, 32 depends on whether gates 38, 40 are open or closed. Thus, in some embodiments, airflow can be directed into either tube, both tubes, or neither tube, and a similar control of airflow through particular tubes can be accomplished in embodiments having more than two tubes. However, alternative embodiments do not utilize such gates (or their alternatives). Instead, air forced through the device during inhalation or exhalation flows through all tubes present within the device.

Airflow sensors 34, 36 measure the pulmonary airflow caused by inhalation or exhalation of air through respiratory port 20. The airflow can be measured based on parameters of the air, for example (and without limitation) pressure, volume, temperature, or a combination of these characteristics. A number of different airflow sensors can be utilized in the device. For example, U.S. Pat. No. 5,562,101 discloses a ceramic transducer with pressure ports connected via tubing to a pressure sensor. The pressure sensor is used to generate a pressure signal indicative of the pressure drop developed across the transducer. The pressure signal can be correlated to airflow, such as by the methods described in U.S. Pat. No. 5,562,101. Another type of airflow sensor is described in U.S. Pat. No. 6,190,326, which utilizes a set of hot wires that can measure several parameters of airflow, including airflow direction. Yet another type of airflow sensor utilizing a venturi is disclosed in U.S. Pat. No. 4,736,750, and an electromechanical airflow sensor is disclosed in U.S. Pat. No. 5,277,195. Additionally, U.S. Pat. No. 5,137,026 describes another airflow sensor based on a differential pressure transducer. Thus, each of these airflow sensors, as well as other sensors capable of measuring airflow, can be considered a pulmonary airflow sensor.

Since airflow can be directed into either or both of tubes 30, 32, the device allows separate or redundant measurements of airflow. Considerations for accurately gathering measurements from a spirometer are discussed in the Background Art of U.S. Pat. No. 5,562,101. For example, insufficient or excessive airflow through a tube of a given diameter can result in significant errors in measuring that airflow. Therefore, multiple tubes of different diameters within the same device allow airflow from a single inhalation or exhalation to be measured in tubes having different ranges of measurement accuracy. In one exemplary embodiment of the device sized for human use, first airflow tube 30 and sensor 34 can most accurately measure airflow rates of between about 0.2 and about 2 liters per second, while second airflow tube 32 and sensor 36 can most accurately measure airflow rates of between about 1 and 5 liters per second. If the person blows into the device at a rate of 1.1 liters per second, then accurate airflow measurements can be taken within each tube, and these measurements can be compared or averaged.

However, if the airflow rate falls outside the range of optimal accuracy for a particular sensor within a particular tube, then the airflow to that tube can be cut off and shunted to another tube. Alternatively, data from an inaccurate tube can be disregarded. For example, data gathered by an airflow sensor can be compared to a pre-programmed range of optimal accuracy for airflow through that tube; if the airflow rate measured by the airflow sensor falls outside the range of optimal accuracy, that data set can be ignored.

The range of optimal accuracy for a tube having a particular diameter can be determined mathematically, statistically, or through testing and calibration. As just one example, a stream of air having a known and constant rate of airflow can be directed into a tube and the airflow rate detected by the airflow sensor can be compared to the actual airflow rate. The range of optimal accuracy can be set according to a particular use or embodiment of the device. For example, the optimal range of accuracy can be that range of airflow rates where the detected airflow rate is within about ±10% of the actual airflow rate.

Figure 6:
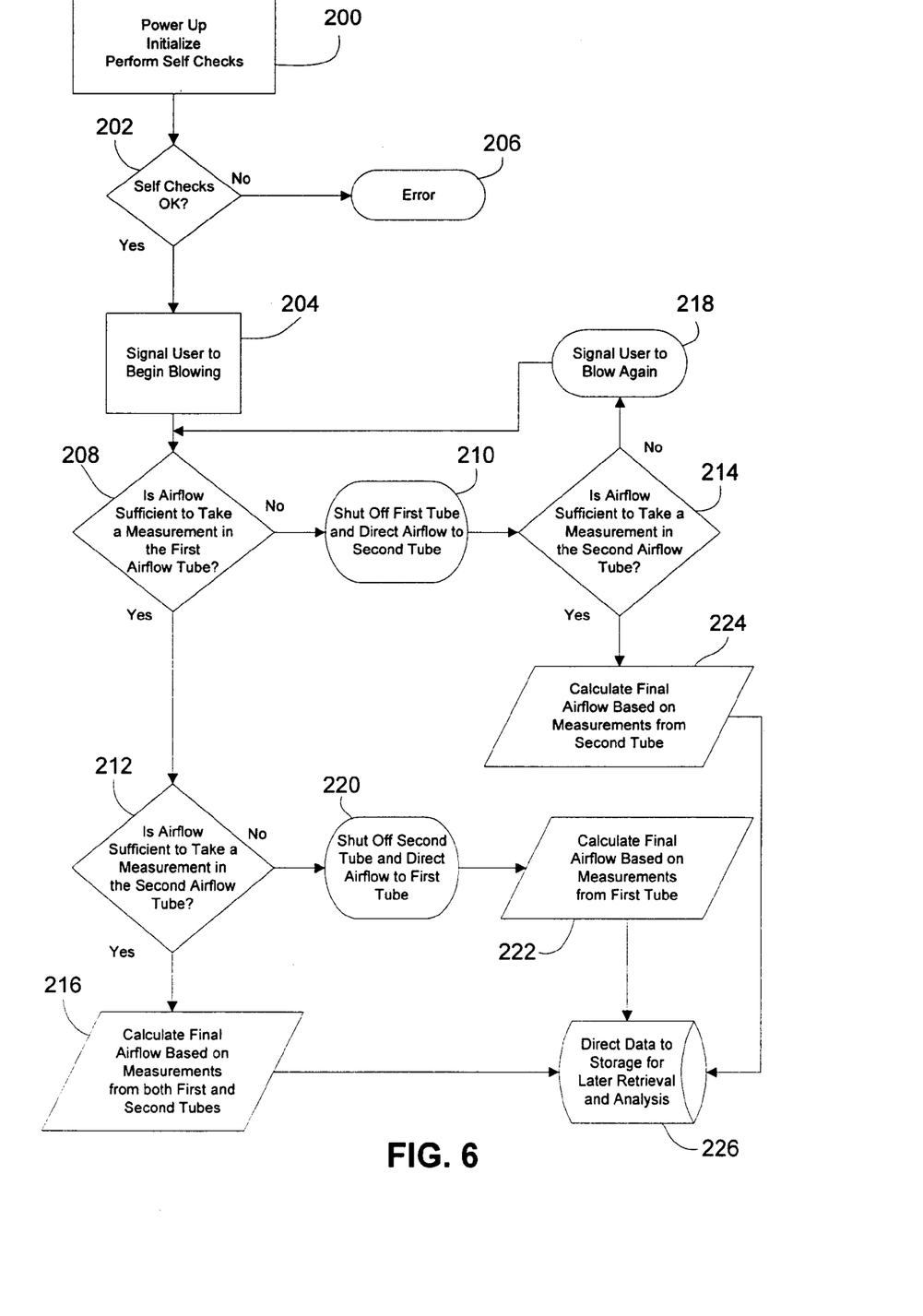
FIG. 6 is a flow chart illustrating the operation of one embodiment of the device by a human.

Continuing the above example, if the person blows into the device at a rate of 3 liters per second (above the range of optimal accuracy for measuring airflow in the first airflow tube), this airflow rate would be detected by airflow sensors 34, 36, which would then be checked against the pre-programmed range of optimal accuracy for each tube. Since the rate of 3 liters per second is greater than the range of optimal accuracy, gate 38 would shut, thus closing first airflow tube 30 and forcing all the blown air into second airflow tube 32, which has an range of optimal accuracy encompassing the detected airflow rate. Alternatively, such as in an embodiment that lacks an airflow director, data from the first airflow tube can simply be disregarded. In a similar manner, if the person blows into the device at a rate of 0.5 liters per second (below the range of optimal accuracy for measuring airflow in the second airflow tube), then gate 40 would be shut in response, thus forcing all the blown air into first airflow tube 30, which has an range of optimal accuracy encompassing that airflow rate, or data generated by airflow sensor 36 within second airflow tube 32 can be disregarded. FIG. 6 illustrates this type of operation. While FIG. 6 illustrates an algorithm for operating one particular embodiment of the device, other algorithms for operating the device are possible and any particular mode or process of operation can depend on factors such as the particular embodiment of the device and its intended uses. Furthermore, operation of the device can be controlled electronically using a microcontroller or microprocessor, such as a microprocessor disclosed herein.

In FIG. 6, operation of the device begins with a power up and initialization phase 200, where the device performs a series of self checks after being turned on. At decision point 202, if the self-checks are suitable, the device signals the user to begin blowing 204 via a visual or audible signal. If the self-checks 202 fail, then the device enters an error mode 206.

After the user begins blowing into the device, the microprocessor (or other data processor) checks the detected airflow in the first tube against the pre-programmed range of optimal accuracy for the first tube to assess whether the airflow is sufficient to take an accurate measurement of airflow in the first tube 208. "Sufficient" airflow is understood to be a rate of airflow falling within the range of optimal accuracy for a tube. Airflow that falls outside this range of optimal accuracy is considered insufficient. If the airflow rate in the first tube not sufficient, then the microprocessor sends a signal to the gate within the first airflow tube, causing it to shut and redirect the airflow solely into the second tube 210. If the airflow rate is sufficient, no signal is sent to the gate and the gate remains open, allowing airflow through the first tube.

In either case, the microprocessor then detects whether the airflow through the second tube is sufficient to take a measurement 212, 214. If the airflow through both tubes is sufficient, then the microprocessor calculates the final airflow based on measurements from both tubes 216. If the airflow is not sufficient in either tube, then the user is instructed to blow again 218 and the microprocessor returns to the point of detecting whether airflow through the first tube is sufficient to take a measurement of the airflow rate in the first tube 208.

If the airflow through the first tube was sufficient, but the airflow through the second tube is not sufficient, the microprocessor sends a signal to the gate in the second tube, causing the gate to shut and the airflow from the mouthpiece to be directed entirely into the first tube 220. The final airflow is then calculated based on measurements from the first airflow tube 222. If the airflow through the first tube was not sufficient to take a measurement of the airflow rate, but was sufficient through the second airflow tube, then the final airflow is calculated based on measurements in the second tube 224. After the final airflow is calculated 216, 222, 224 the airflow data is directed to storage for later retrieval and analysis 226.

Figure 7:
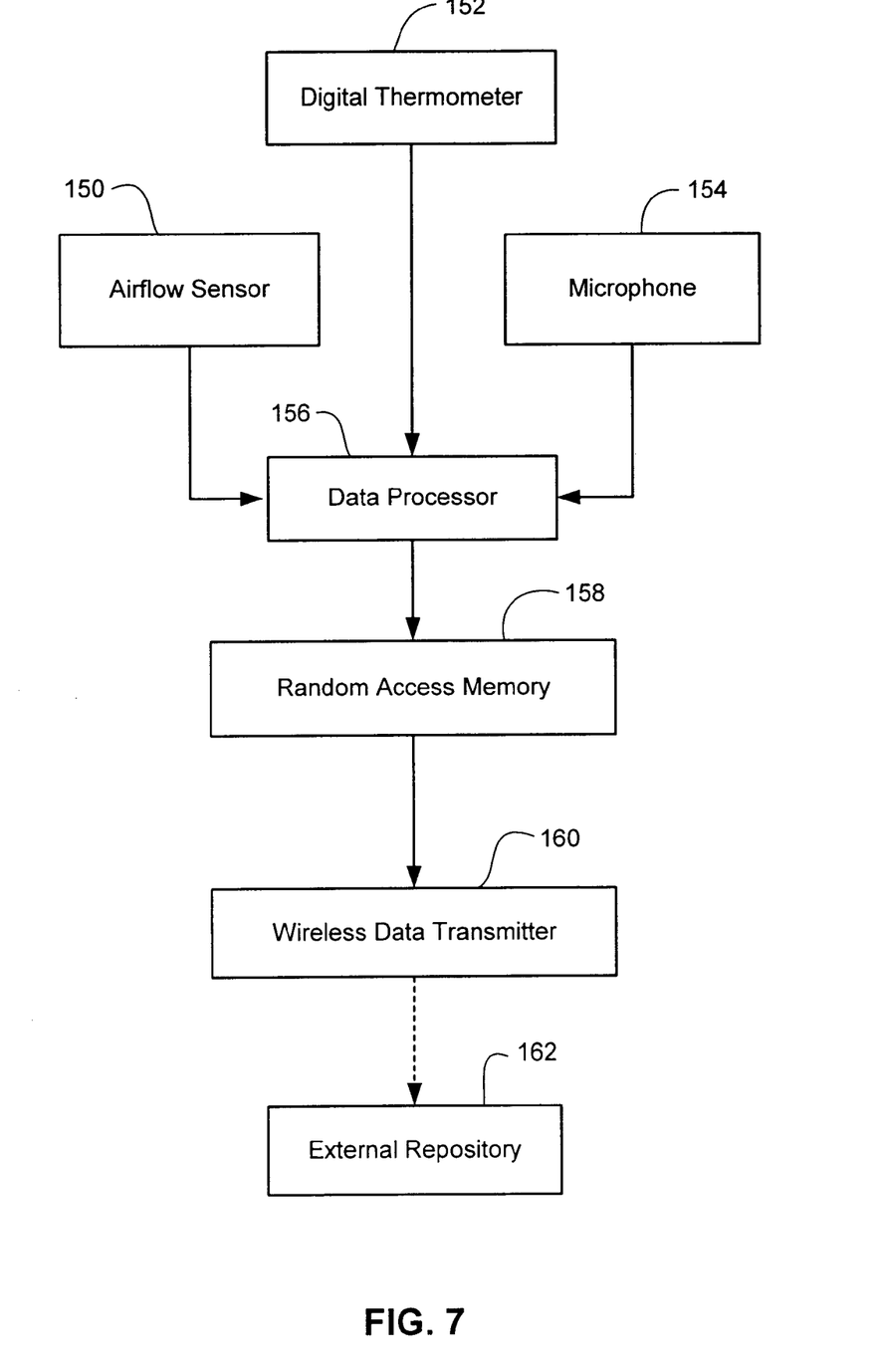
FIG. 7 is a schematic block diagram illustrating one embodiment of the device. The lines indicate operable connections among different parts of the device. Arrows indicate the direction of data transfer, and the dotted line indicates transmission of data collected and processed by the device to an outside repository.

In alternative embodiments of the device lacking an airflow director, steps 210 and 220 can be eliminated from the algorithm illustrated in FIG. 7. For example, at step 224, the microprocessor can calculate the final airflow based on measurements from the second tube alone and essentially ignore any data based on measurements from the first tube, while at step 222, the microprocessor can calculate the final airflow based on measurements from the first tube alone and essentially ignore any data based on measurements from the second tube.

The device optionally may include a thermometer or other temperature sensor in the housing lumen and/or tubes. For example, as shown in FIG. 1, digital thermometers 42, 44 are located within airflow tubes 30, 32. In alternative embodiments, the temperature sensor is another type of thermometers, a thermocouple, a thermistor, or any other suitable device. For example (and without limitation), the illustrated digital thermometers 42, 44 measure the temperature of the user's breath, which can then be used to estimate body temperature. In alternative embodiments, however, body temperature is measured by a temperature sensor mounted outside the airflow path or otherwise coupled to the device. For example, a temperature sensor can be mounted to the mouthpiece at the proximal end of the device for measuring the temperature of the user's lips, or a separate temperature sensor can be placed on the user's body, such as on the forehead, and operably connected to the device. As another example, the mouthpiece can include an infrared thermometer for detecting the user's body temperature based on infrared signatures within the interior of the mouth, such as a modified version of the tympanic infrared thermometer disclosed in U.S. Pat. No. 6,149,297. In still other alternative embodiments, temperature sensor measures the ambient temperature outside the device, rather than the body temperature of the subject. For example, the temperature sensor can be a thermocouple or digital thermometer coupled to the housing in a way that allows the ambient temperature to be measured. The temperature sensor can be coupled to or correlated with the pulmonary airflow sensor to provide integrated data collection from both sensors.

The device also can include a non-spirometric cardiopulmonary activity sensor, such as cardiovascular or pulmonary activity detectable by other than airflow. For example, the non-spirometric cardiopulmonary activity sensor can utilize acoustic, optical, tactile, electrical, or other sensors to detect or measure a parameter or characteristic of cardiovascular or pulmonary activity, including (but not limited to) blood pressure, heart rate, patterns of heartbeat, blood gas concentration (for example, using an oximeter to measure blood oxygen concentration), concentration of gases in the breath during exhalation (for example, using a detector of a specific gas, such as oxygen, nitric oxide, carbon dioxide, or a combination thereof), respiratory pattern or rate, temperature of the breath during exhalation, and lung sounds.

Figure 4:
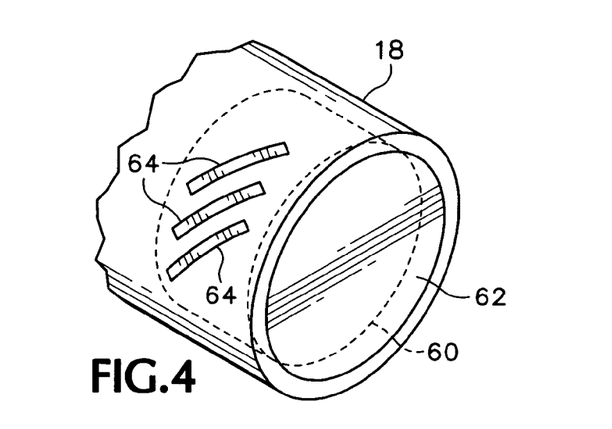
FIG. 4 illustrates a perspective view of the distal end of the embodiment illustrated in FIG. 1.

One specific example of a a non-spirometric cardiopulmonary activity sensor is a pulse rate sensor, such as microphone 60 illustrated in FIGS. 1 and 4. Microphone 60 is located adjacent the distal end of device 10 and is capable of detecting the sounds of the subject's heartbeat. Once mouthpiece 12 is placed in the subject's mouth, microphone 60 detects sound signatures matching a frequency and amplitude range associated with transmission of heart sounds from the chest cavity through the throat and mouth of a subject. For example, U.S. Pat. No. 6,241,683 describes detection of respiratory sounds and how such sounds can provide a diagnosis and/or prognosis of respiratory disease. One feature described in that patent involves the digital filtering of sound signals between 200 and 1000 Hz in order to remove heart and muscle sounds, which are typically less than 200 Hz. Therefore, the sound data collected by microphone 60 can be filtered to amplify sound signals less than 200 Hz in order to differentiate heart and muscle sounds from respiratory sounds. Detection of such sound signatures can be conducted before, during, or after the subject inhales or exhales through mouthpiece 12.

Alternatively, distal end 24 of device 10 can be placed against the chest of the subject for recording heart beat through microphone 60, or microphone 60 can be replaced by a remote microphone operably connected to the device via a wire lead and a microphone jack or a wireless connection.

In addition to measuring heart rate, microphone 60 can detect and/or record sounds of breathing, such as raspiness, wheezing, secretion, or rales within the lungs. Detection of such breath sounds during assessment of lung function can assist in other medical or veterinary determinations, such as diagnosing disease, assessing the physiological status of the subject, or determining drug efficacy. For example, wheezing is associated with asthma, and changes in wheezing detected by the sensor can be used as a parameter to measure responses to therapeutic intervention, such as administration of an anti-asthmatic medication. The presence of pulmonary rales (crackling), associated with heart failure, can also be used as an additional piece of diagnostic data to differentiate a purely pulmonary condition from a pulmonary complication of an underlying myocardial compromise.

In some embodiments, the device is pre-programmed to detect sounds of a particular frequency, amplitude, and/or duration associated with pulmonary diseases or disorders. In other embodiments, the sounds detected by the microphone are digitally recorded and stored within the device for later analysis by a health care professional. For example, devices for recording and/or analyzing breath sounds are described in PCT publications WO 90/04945 and WO 99/52431, and U.S. Pat. Nos. 6,383,142; 6,241,683; and 6,168,568.

In other embodiments, the non-spirometric cardiopulmonary activity sensor includes a heart monitor. For example, a simple heart monitor can include plural electrocardiogram (EKG) electrodes operably connected to the data processor of the device to allow integrated collection of pulmonary airflow information and data related to the subject's heartbeat, such as heart rate or abnormalities in heart rhythm.

In still other embodiments, the non-spirometric cardiopulmonary activity sensor includes a blood oximeter, such as non-invasive blood oximeter, for example, an infrared blood oximeter.

Additionally, in still other embodiments, the non-spirometric cardiopulmonary sensor is a device that detects or monitors exhaled breath components, including gases. For example, a nitric oxide (NO) detector is disclosed in Shioya, T. and Swager, T. M., Chem. Comm., 1364–65 (July 2002). This detector is a small transistor carrying an electrically conductive molecular polymer studded with cobalt ions. NO molecules bind to the cobalt ions and alter the conductivity of the polymer, which is then detected by the transistor. As another example, PCT publication WO 02/17991 describes a portable respiratory gas sensor capable of measuring the concentration of a particular respiratory gas (for example, NO or oxygen) or other breath component (such as glucose) in the exhalation flow pathway of a subject.

As illustrated in FIG. 4, microphone 60 includes an optional fabric cover 62 stretched over housing lumen 22 and airflow port 24 to protect the microphone parts within housing lumen 22. The spaces within the weave of fabric cover 62 allow air to flow from housing lumen 22 out through airflow port 24. Additionally, airflow port 24 includes an optional set of lateral vents 64 in fluid communication with housing lumen 22 to permit additional airflow through airflow port 24. While the three illustrated lateral vents 64 are rectangular in shape, vents of other shapes or sizes are possible, such as arcuate, circular, triangular, hexagonal, or rhomboid lateral vents. Also, a different number of lateral vents can be defined in the housing, such as one, two, four, five, six or more lateral vents. In alternative embodiments, the distal end of the housing lumen does not have the protective fabric cover and/or the lateral air vents.

Microphone 60 can be used to detect other physiological sounds in the subject's body and those sounds can be stored in digital memory for later analysis. For example, microphone 60 can be placed against the subject's abdomen for recording gastrointestinal sounds, or microphone 60 can be replaced with an equivalent microphone in remote connection (for example, by a wireless connection or through a wire lead) to the device, and the remote microphone can be placed against the subject's abdomen. Similarly, microphone 60 (or its equivalent) can be placed elsewhere on the subject's body, such as on a joint for detecting popping or grinding within the joint. As another example, microphone 60 (or its equivalent) can be placed over a blood vessel, such as the major blood vessels of the neck, to detect blood flow through the vessel. Abnormal blood flow sounds, or differential blood flow through similar vessels (for example, the right and left carotid arteries), can indicate an obstruction of a blood vessel, such as atherosclerosis or a blood clot.

Additionally, microphone 60 can record dictation from the subject or other user of the device, such as a health care professional. For example, a subject using the device at home can record information about the date and time of use, or the subject can relate basic information related to the use of the device, such as recording a short note like "I feel dizzy now," or "My heart feels like it is beating faster." As another example, a physician using the device in a clinic can record notes about the patient and transfer those notes with the data later transmitted by the device.

In addition to the microphone, device 10 can include an optional signaler, such as a small speaker, one or more warning lights (such as LED's), an LCD screen, or other mechanism for providing a visual or audible signal to the user. In particular embodiments, the signaler is an LCD screen on the external surface of the device that can display particular pre-programmed messages. In other particular embodiments, the signaler is a small speaker that can audibly transmit messages stored as pre-programmed digital audio files. For example, the signaler can include pre-programmed messages for operating the device or performing a PFT, such as "Error—failure during initialization—please restart," or "Blow harder," "Blow softer," "Blow as hard as you like," or "Keep blowing until your lungs feel empty." In still other embodiments, the signaler is a plurality of different colored LEDs and a guidebook that includes messages corresponding to the pattern of lit or unlit LEDs.

In some embodiments, device 10 also includes a light source (not shown) mounted on the outside of housing 14 or located within housing lumen 22, which can be used to illuminate the inside of the subject's mouth and throat. For example, a physician or veterinarian using the device on a subject could obtain cardiopulmonary data about the subject, then use the light source to examine the interior of subject's mouth and throat. Any suitable light source can be used, such as a light bulb or LED.

In certain embodiments, the device includes, or is coupled to, a digital camera or digital video camera. As just one example, an optical fiber with a lens can be mounted within the housing lumen, passed through the wall of the housing, and coupled to a digital camera located outside the device. Using such embodiments, digital images of the interior of the subject's mouth and throat can be acquired before, during, or after the device is used to gather cardiopulmonary data from a subject. These digital images can provide additional information about the subject's physiological condition.

In some embodiments, the device includes a removable prophylactic cover, such as a snugly fitting plastic film or bag, to enhance the sterilization of the device, or to resist dirt and other contaminants. For example, embodiments used in hospitals can utilize replaceable mouthpieces, which are disposed after each use by a patient, and the replaceable prophylactic cover over the housing to inhibit transmission of viruses and bacteria among patients. As another example, embodiments used by veterinarians in the field can employ replaceable covers to inhibit contamination by dirt, mud, or animal body fluids and to assist in cleaning the device—a soiled cover can simply be removed and replaced by a clean one.

FIG. 6 illustrates one embodiment for integrating or collating data obtained by various sensors within the device. In this embodiment, pulmonary airflow sensor 150, temperature sensor 152, and non-spirometric cardiopulmonary activity sensor 154, are operably connected to a data processor 156.

The dataprocessor 156 include a digital microprocessor, microcontroller, central processing unit, or other digital processing device. Particular examples of data processor include the line of Motorola MPC8XXX Integrated Host Processors (Motorola, Inc., Shaumburg, Ill.); the AMD Athlon™ XP, Athlon™ 4, and Duron™ processors (Advanced Micro Devices, Inc., Huntsville, Ala.); and the Mobile Intel® Pentium® 4 Processor-M, Mobile Intel® Pentium® III Processor-M, and Intel® Mobile Celeron® processors (Intel Corporation, Hillsboro, Oreg.).

The data processor, such as a microprocessor, allows integrated collection of data from all sensors within the device. For example, as illustrated in FIG. 6, data regarding pulmonary airflow (collected via the airflow sensor), the subject's body temperature (obtained via the digital thermometer), and non-spirometric cardiopulmonary activity, such as cardiac pulse rate (obtained via the microphone), can be integrated into a single data set.

Integrated data collection offers the advantage of measuring a subject's pulmonary function and some other physiological characteristic simultaneously, or nearly simultaneously, to provide a faster or more accurate physiological assessment of the subject. Since cardiovascular and pulmonary functions are interrelated, collecting and integrating data from each system can assist in the diagnosis of disease or conditions affecting the vascular system and lungs.

Additionally, measuring body temperature can provide information that alters conclusions based on spirometric data alone or in combination with non-spirometric cardiovascular information. For example, the presence of both a fever and abnormal spirometric data indicating reduced lung function can signal an acute infection, such as pneumonia, while the lack of a fever can indicate some non-infectious disease, such as emphysema. Acute infection can be assessed using other devices or methods. For example, nitric oxide (NO) is produced when a subject's immune system fights infection. Therefore, detecting increased NO levels in a subject's breath can signal infection, such as pneumonia or exposure to a biological-warfare agent.

The importance of the diagnostic interrelationship of spirometry and non-spirometric data is illustrated, for example, by a subject (such as a human patient) who presents with shortness of breath. Such a symptom in an individual with pre-existing asthma or COPD is sometimes mistakenly diagnosed as an exacerbation of the underlying pulmonary condition, when in fact it is a myocardial problem, such as heart failure. However, by monitoring both spirometric and non-spirometric data, such as heart sounds or electrocardiographic data, such an incorrect diagnosis can be avoided and appropriate (and often life-saving treatment) initiated. For example, if shortness of breath is caused by heart failure with pulmonary edema in a person with pre-existing asthma, a diagnosis of heart failure can be detected by the presence of an S3 and/or S4 heart sound detected by the microphone. Alternatively, EKG changes associated with myocardial ischemia can detect an underlying myocardial condition that may present as shortness of breath.

The diagnostic interrelationship of spirometry and non-spirometric data also is illustrated by a subject having other breathing difficulties, such as hyperventilation. For example, lower blood oxygen concentration in healthy patients will signal the central nervous system to stimulate the lungs and induce a higher respiratory rate. Therefore, combining blood oximetry and spirometry data can indicate a problem of the central nervous system of a patient with low blood oxygen concentration and low respiratory rate. Tachycardia (variations in heart rate) is often seen in patients who are hypoxic. Collecting spirometric data and measuring heart rate at the same time can help ascertain whether the tachycardia and hypoxia are due to a pulmonary obstruction (such as asthma detected by decreased $FEV_1$), or some non-pulmonary cause for hypoxia, (such as anemia or reduced oxygen carrying capacity of the blood). As another example, an embodiment of the device having a blood oximeter (such as a pulse oximeter or other sensor that measures oxygenated hemoglobin in blood) can integrate pulmonary airflow data with blood oxygen saturation data to measure the efficiency of oxygen absorption through the lungs into the blood. Low efficiency of absorption (as reflected in a low blood oxygen saturation, such as a saturation of less than about 95% or 90%) can indicate an obstruction in the lungs, apnea, or other condition inhibiting oxygen uptake. As still another example, detecting blood gas concentrations or respiratory gas concentrations can differentiate different diseases or conditions, such as anxiety, induced hyperventilation, asthma, infection, COPD, respiratory alkalosis, or drug overdose (which can inhibit respiratory drive and induce apnea). In another example, excessive loss of $CO_2$ in exhaled air can indicate hyperventilation and associated respiratory alkalosis.

Once collected and/or integrated, the data can be transferred to data storage 158, such as the random access memory (RAM) illustrated in FIG. 6. Other types of data storage include a removable memory card, such as a flash memory card, or a small hard drive. In alternative embodiments, the data storage is located apart from the device and the device is operably connected to the data storage. For example, and without limitation, the data storage can be an external disk drive, CD-RW drive, or DVD drive in wireless connection to the data processor, or the device can include a data port for connecting the data processor to external data storage via a cable or other wired connection.

Additionally, the data storage can include a set of preprogrammed parameters. For example, a unique identifier for a particular patient can be preprogrammed into a set of read-only memory (ROM). After data is collected and stored within the device, such as being stored within internal RAM, the preprogrammed information can be transmitted along with the collected data. In addition to the unique identifier, pre-programmed information can include any other useful information, such as a timestamp that records the date and time of each use of the device; information about the device features, model and manufacturer; calibration data; or physiological and demographic details about the user, for example, age, height, weight, gender, residence address, citizenship, past medical conditions, or occupation.

Data collected by the device can be securely stored by the device or some external repository. For example, the data can be password protected, or the device itself can be programmed to require a password prior to operation. In particular embodiments, the data is encrypted during or after collection.

Figure 5:
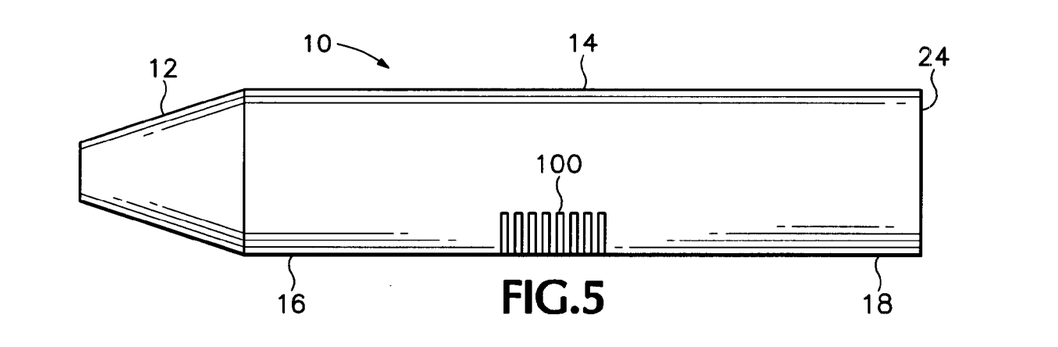
FIG. 5 illustrates an external view of another embodiment of the sensor device.

Also shown in FIG. 6 is data transmitter 160 that transfers data from the device 10 to an external repository 162. The specific data transmitter 160 chosen for a particular embodiment can depend on several factors, such as the sophistication of the user, the environment in which the device will be used (for example, a clinical setting versus home use), the equipment and technology available for connecting the device to the external repository, and the amount of data expected to be transferred. In the embodiment illustrated in FIG. 1, data transmitter 160 is a wireless data transmitter (not shown), such as a radiofrequency or infrared (IR) data transmitter. Alternative embodiments utilize other types of data transmitters, such as a wire or cable directly connecting the device to the external repository or a docking station for the device where the docking station is itself connected to the external repository. FIG. 5 illustrates such an alternative embodiment showing device 10 with docking interface 100 adapted from the docking interface of a Handspring™ Visor Platinum (Handspring, Inc., Mountain View, Calif.) handheld organizer. The embodiment illustrated in FIG. 5 is placed in its associated docking station (not shown), which is connected to a computer, for transfer of its data to the computer in a manner similar to the synchronization operation of Handspring™ Visor Platinum.

In some embodiments, the external repository is a standalone computer, such as a laptop, handheld, or portable computer, or a network server. For example (and without limitation), the device can be used in a hospital setting with a nurse or clinician carrying a handheld or laptop computer wirelessly connected to the device. The nurse or clinician can obtain cardiopulmonary data from several individual patients, store the information in the handheld computer, and later download this information to the hospital's centralized patient database. Alternatively, the device can be wirelessly connected to a central server on the hospital's computer network, and the information collected by the nurse or clinician can be transferred directly to that server and incorporated into the centralized patient database. As another example, a person can use the device at home to collect physiological information over a period of time, such as a few days, a week, a month, or even longer. That person can connect the device to a home computer (via a wireless connection, a docking station, a data cable, or other suitable connection) and download the data from the device to the home computer.

In alternative embodiments, the external repository is a database housed on a larger computer network, such as a wide area network (WAN) or the Internet. For example, a person using a device at home as part of a clinical trial or treatment regimen can transmit data from the device directly to a clinician over the Internet via email or to a centralized database via an Internet browser interface. As another example, a person with a pulmonary disorder undergoing evaluation or a treatment regimen can use the device during daily activities, then transmit data from the device to an Internet database via a home computer. If the device is designed for use with a docking station (similar to the embodiment illustrated in FIG. 5), the user can connect the docking station to a home computer, establish a connection from the computer to the Internet, place the device in the docking station, and transmit data from the internal memory of the device to a centralized database on an Internet server or other host computer.

In some embodiments, a software interface for downloading data from the device is included as part of the external repository. For example, in the clinical embodiment described above, the handheld or laptop computer carried by the nurse (or other clinician) can include an interface for connecting to a patient's device, downloading the data stored on the device, and organizing the data once it is transferred to the computer. As another example, a person independently using the device can load a similar interface onto a home computer. Using the interface, he can then establish a data connection between a computer and the device (for example, through a docking station), establish another connection between a computer and a remote computer or database (for example, over the Internet), and transfer the stored data from the device to that remote computer or database. In addition to providing instructions for using the device and transferring data to an external repository, the software interface can include a feature to allow programming and storage of information, such as a unique identifier and patient information. Such programming provides an alternative to programming information into ROM housed within the device, as described above.

The device can be used in any appropriate setting to gather physiological information about a subject. In some embodiments, the device is used in a hospital (including a veterinary hospital) or other clinical setting for gathering relevant health information about a subject. In particular embodiments where the subject is incapable of personally using the device (for example, an unconscious human patient or dog in a veterinary hospital), the mouthpiece of the device can be altered to include a facial mask for fitting over the nose and/or mouth of the subject, or the mouthpiece can be designed to be adapted to a preexisting facial mask. Conscious human subjects can be instructed to use the device independently, or a nurse or other clinician can visit a patient periodically with the device. In the case of unconscious or infirm subjects, or non-human subjects, devices with mouthpieces adapted to fit breathing tubes or masks can be operated by nurses or other clinicians to obtain cardiopulmonary data from those subject.

In other embodiments, the device is used outside a clinical setting, such as part of a program for monitoring or treating a pulmonary condition or disease. For example, the device can be used to periodically monitor a person at risk for developing cystic fibrosis, or to monitor the response of an asthmatic person to a particular medication or other treatment. The collected information can be analyzed to determine the onset of cystic fibrosis or effectiveness of an asthma medication based on the person's heart rate, respiratory rate, and spirometric performance (for example, FVC, PEF, and $FEV_1$).

In some embodiments, the device provides feedback information during, or soon after, administration of a medication. For example, the device can be used by a hospitalized person during intravenous administration a drug to treat pleursy. Detection of increased airflow and reduced rales can indicate that the drug is having some effect on the pleursy.

In particular embodiments, the device includes, or is operably coupled to, an applicator for administration of a medication or other bioactive composition, such as a metered dose inhaler (MDI), a transdermal applicator, or other device capable of administering a composition to the subject. For example, an embodiment of the device which includes an MDI in fluid connection with the housing lumen can be used to both administer an asthma medication (during inhalation) and monitor the effectiveness of that medication based on changes in cardiopulmonary status. For example, if a dose of a beta antagonist is administered to an asthma patient, and $FEV_1$ does not subsequently improve in a clinically significant manner, then a subsequent dose of medicine can be administered from the MDI, as long as the dosage does not exceed a predetermined maximum dosage. As another example, the bio-sensor can be operably coupled to a digitally controlled composition delivery device. For example, U.S. Pat. Nos. 5,894,841 and 6,196,218 describe dispensers for inhalational administration of a bioactive composition. As another example, U.S. Pat. No. 6,165,155 describes a low-profile automatic drug delivery system for transdermal or subcutaneous delivery of a bioactive composition. In such an embodiment, cardiopulmonary data about a subject is collected by the bio-sensor and digitally transferred or transmitted to the delivery device. The delivery device then uses the data, transferred or transmitted by the bio-sensor, to control the administration of a bioactive composition, such as a medication. Based on the cardiopulmonary data transmitted by the bio-sensor, the delivery device can alter the delivery of the composition—for example, by changing the rate of delivery, total amount delivered, method of delivery, or particle size of the composition delivered—during administration of the bioactive composition. Thus, the combination of the bio-sensor and delivery device offers the capability to collect bio-feedback information (by the bio-sensor) during or following administration of medication or other bioactive composition (by the pulmonary delivery apparatus).

Alternatively, the device can be used to collect baseline data for comparison with data obtained from different subjects, or data obtained from the same subject at a later time, such as later in the subject's life. Thus, data obtained via the device can be pooled, such as data obtained from a single subject over time or data obtained from multiple subjects.

In some embodiments, the device serves as an easy-to-use diagnostic tool. For example, a person using the device at home can transmit cardiopulmonary data, which is encrypted to protect the person's privacy, over the Internet to a centralized database. That data can be compared to baseline data obtained from other people—even several hundred or thousand or million people. A diagnostic report based on that comparison, including instructions to consult with a medical professional, can then be sent back to the user via mail, email, or facsimile. Alternatively, the device can include instructions to telephone a consultant who would relate the results of the report. As another example, the device can be preprogrammed to alert the user to seek medical advice if the collected data meets certain criteria, such as wheezing and low breathing rate coupled with a high body temperature, which could indicate infection in the lungs.

The data collected by the device can be archived for long-term analysis. Data from a single subject or multiple subjects obtained repeatedly over a period of time (for example, several days, weeks, months, or years) can be archived and periodically analyzed to detect any abnormalities. This archival feature provides the benefit of detecting a decline in pulmonary ability that might otherwise go unnoticed, or can be used in clinical trials to measure and track the efficiency of a drug. For example, a person with an upper respiratory infection or influenza can take daily or twice-daily measurements of cardiopulmonary function, and transfer the collected data via the Internet to a centralized database. This collected data can then be periodically analyzed, by a human or software agent, to detect a downward trend in pulmonary function. If the person's lung function (measured via spirometric data) falls beneath a certain threshold, a warning can be delivered to that person and/or the person's physician (such as via email) stating that the person should seek additional medical attention (for example for possible pneumonia). While the person might not notice a gradual decline in breathing ability or a gradual increase in body temperature, trend analysis of the archived cardiopulmonary data obtained from the subject can provide an early indicator of a decline in cardiopulmonary function caused by infection, chronic disease, or other physiological condition. Furthermore, data from multiple subjects can be obtained over time, archived, and later analyzed for population trends, such as trends within a population of subjects expected to be at a higher risk for developing a cardiopulmonary disease or condition, such as a respiratory disease. For example, cardiopulmonary data periodically obtained from persons living near a smelter, refinery, or living in some other industrial area, can be archived in a database and several years of data can be analyzed to detect trends in the development or exacerbation of asthma or other respiratory disease. As another example, livestock populations (such as cattle and horses) near wildlife populations (such as deer and elk) can be periodically monitored with the bio-sensor to detect early signs of disease transmission from wildlife. The bio-sensor offers a non-invasive method of collecting cardiopulmonary data from a large population of livestock. Those animals exhibiting signs of infection (such as fever and/or impaired respiration) can then be identified for further, more specific tests, such as blood tests that detect antigens to specific infectious agents.

Additionally, data collected by a number of devices can be integrated into a database for further processing. For example, data from a population of human users can be collected into a large database and later mined for particular trends or clusters of information. In specific embodiments, a database is coupled to analysis software to provide an expert system for guiding clinicians. For example, a person using the device at home while recovering from a pulmonary embolus could transmit data collected by the device to a centralized database. Analysis software would then process this transmitted data, compare it against information in the large database, and transmit a report on the person's general health to the person's treating physician.

The sensor device for sensing cardiopulmonary activity, as described above, can be made or manufactured in any appropriate manner. In some embodiments, an elongated housing having a proximal end, a distal end, and a lumen is obtained, and an airflow sensor is mounted inside the housing lumen. A data processor, such as a microprocessor, is added and coupled to the airflow sensor. A non-spirometric cardiopulmonary activity sensor also can be added to the housing and operably coupled to the data processor. Such a sensor device is then capable of integrated collection of cardiopulmonary data obtained via the airflow sensor and the non-spirometric cardiopulmonary activity sensor.

In some embodiments, the method of making or manufacturing the sensor device includes adding other features described above. For example, plural airflow tubes, such as a first airflow tube and a second airflow tube, can be displaced within the housing lumen. As described above, the diameters of the plural airflow tubes may be identical, substantially similar, or different. As another example, a temperature sensor can be coupled to the data processor. Such a device is capable of integrated collection of physiological data obtained via the airflow sensor, the cardiopulmonary activity sensor, and/or the temperature sensor.

Having illustrated and described the principles of the invention by several embodiments, it should be apparent that those embodiments can be modified in arrangement and detail without departing from the principles of the invention. Thus, the invention includes all such embodiments and variations thereof, and their equivalents.

We claim:

1. A sensor device for obtaining physiological information, comprising:
   an elongated housing having a proximal end, a distal end, and a lumen, wherein the proximal housing end defines a respiratory port that is in fluid communication with the lumen;
   an airflow port defined in the wall of the housing adjacent the distal end, wherein the airflow port is in fluid communication with the lumen and the respiratory port, and the lumen defines a passageway that allows air to flow from the airflow port to the respiratory port during inhalation and from the respiratory port to the airflow port during exhalation;
   means for measuring pulmonary airflow housed within the passageway of the lumen;
   means for measuring non-spirometric cardiopulmonary activity housed within the passageway of the lumen; and
   means for processing data operably coupled to both the means for measuring pulmonary airflow and the means for measuring non-spirometric cardiopulmonary activity, wherein the sensor device is capable of integrated collection of data obtained via the means for measuring pulmonary airflow and means for measuring non-spirometric cardiopulmonary activity.

2. The sensor device according to claim 1, wherein the means for measuring pulmonary airflow comprises an electronic airflow sensor.

3. The sensor device according to claim 1, wherein the means for measuring non-spirometric cardiopulmonary activity comprises a microphone, blood oximeter, or heart monitor.

4. The sensor device according to claim 1, wherein the means for processing data comprises a microprocessor.

5. The sensor device according to claim 1, wherein the device is dimensioned for use by a human adult or child.

6. The sensor device according to claim 1, further comprising a lateral vent defined in the housing adjacent its distal end, the lateral vent in fluid communication with the housing lumen.

7. The sensor device according to claim 1, further comprising means for transferring data operably coupled to the means for processing data.

8. The sensor device according to claim 7, wherein the means for transferring data is a wireless data transmitter.

9. The sensor device according to claim 1, further comprising means for directing airflow housed within the lumen.

10. The sensor device according to claim 9, wherein the means for directing airflow is disposed between the airflow port and the respiratory port.

11. The sensor device according to claim 1, further comprising means for measuring temperature operably coupled to the means for processing data.

12. The sensor device according to claim 11, wherein the means for measuring temperature is a digital thermometer or infrared thermometer.

13. The sensor device according to claim 11, wherein the means for measuring temperature is capable of measuring the body temperature of the subject.

14. The sensor device according to claim 11, wherein the sensor device is capable of integrated collection of data obtained via the means for measuring pulmonary airflow, the means for measuring non-spirometric cardiopulmonary activity, and the means for measuring temperature.

15. A method for collecting physiological data about a subject, comprising obtaining cardiopulmonary data about a subject via the sensor device of claim 1.

16. The method according to claim 15, wherein the method for collecting physiological data about a subject comprises a method for diagnosing a disease or physiological condition of the subject.

17. The method according to claim 15, wherein the sensor device further comprises means for transferring data operably coupled to the means for processing data, and the method further comprises transmitting the cardiopulmonary data obtained by the device to an external repository.

18. The method according to claim 15, wherein the subject is a human.

19. The sensor device according to claim 1, wherein the sensor device is operably coupled to a means for delivering a bioactive composition.

20. The sensor device according to claim 1, wherein the airflow port is positioned so as to allow expired or inhaled air to flow longitudinally through the airflow port.

21. The sensor device according to claim 1, wherein the means for measuring non-spirometric cardiopulmonary activity comprises a microphone operable to detect a physiological sound of a subject.

22. A sensor device for obtaining physiological information, comprising:
    an elongated housing having a proximal end, a distal end, and a lumen, wherein the proximal housing end defines a respiratory port that is in fluid communication with the lumen;
    an airflow port defined in the wall of the housing adjacent the distal end, wherein the airflow port is in fluid communication with the lumen and the respiratory port;
    means for measuring pulmonary airflow housed within the lumen; means for measuring non-spirometric cardiopulmonary activity housed within the lumen; and
    means for processing data operably coupled to both the means for measuring pulmonary airflow and the means for measuring non-spirometric cardiopulmonary activity, wherein the sensor device is capable of integrated collection of data obtained via the means for measuring pulmonary airflow and means for measuring non-spirometric cardiopulmonary activity;
    wherein the sensor device is operably coupled to a means for delivering a bioactive composition.

23. A sensor device for obtaining cardiopulmonary data, comprising:
    an elongated housing having a proximal end, a distal end, and a lumen, wherein the proximal housing end defines a respiratory port that is in fluid communication with the lumen;
    an airflow port defined in the housing adjacent the distal end of the lumen, the airflow port being in fluid communication with the lumen, wherein expired air flows through the respiratory port, the lumen and the airflow port to atmosphere, and inhaled air flows through the airflow port, the lumen and the respiratory port into a user;
    an airflow sensor positioned within the lumen;
    a non-spirometric cardiopulmonary activity sensor positioned within the lumen; and
    a data processor operably coupled to both the airflow sensor and the non-spirometric cardiopulmonary activity sensor, wherein the sensor device is capable of integrated collection of cardiopulmonary data obtained via the airflow sensor and the non-spirometric cardiopulmonary activity sensor.

24. The device according to claim 23, wherein the non-spirometric cardiopulmonary activity sensor compromises a microphone, blood oximeter, or heart monitor.

25. The device according to claim 23, further comprising a digital or infrared thermometer operably coupled to the data processor.

26. The device according to claim 23, further comprising a data transmitter operably coupled to the data processor.

27. The device according to claim 26, wherein the data transmitter is a wireless data transmitter.

28. The sensor device according to claim 23, further comprising a lateral vent defined in the housing adjacent its distal end, the lateral vent being in fluid communication with the housing lumen.

29. The sensor device according to claim 23, further comprising an airflow director positioned within the lumen.

30. The sensor device according to claim 23, wherein the sensor device is operably coupled to a bioactive composition delivery device.

31. The sensor device according to claim 23, wherein the lumen defines first and second airflow tubes.

32. The sensor device according to claim 31, further comprising at least one airflow director configured to control the flow of air through one or both of the first and second airflow tubes.

33. The sensor device according to claim 32, wherein the at least one airflow director comprises a first airflow director and a second airflow director, wherein the first airflow director controls the flow of air through the first airflow tube and the second airflow director controls the flow of air through the second airflow tube.

34. A sensor device for obtaining cardiopulmonary data, comprising:
    an elongated housing having a proximal end, a distal end, and a lumen, wherein the proximal housing end defines a respiratory port that is in fluid communication with the lumen;
    an airflow port defined in the housing adjacent the distal end of the lumen, the airflow port being in fluid communication with the lumen;
    an airflow sensor positioned within the lumen;
    a non-spirometric cardiopulmonary activity sensor positioned within the lumen; and
    a data processor operably coupled to both the airflow sensor and the non-spirometric cardiopulmonary activity sensor, wherein the sensor device is capable of integrated collection of cardiopulmonary data obtained via the airflow sensor and the non-spirometric cardiopulmonary activity sensor;
    wherein the sensor device is operably coupled to a bioactive composition delivery device.

35. A sensor device for obtaining physiological information, comprising:
    an elongated housing having a proximal end, a distal end, and a lumen, wherein the proximal housing end defines a respiratory port;
    a first airflow tube defined within the lumen and having a first airflow tube diameter, wherein the first airflow tube is in fluid communication with the respiratory port;
    a second airflow tube defined within the lumen and having a second airflow tube diameter, wherein the second airflow tube is in fluid communication with the respiratory port;
    an airflow port defined in the wall of the housing adjacent the distal housing end, wherein the airflow port is in fluid communication with the first airflow tube, the second airflow tube, and the respiratory port; and a pulmonary airflow sensor positioned within the lumen and capable of measuring airflow through the first airflow tube and second airflow tube.

36. The sensor device according to claim 35, wherein the first airflow tube diameter is less than the second airflow tube diameter.

37. The sensor device according to claim 35, further comprising a non-spirometric cardiopulmonary activity sensor.

38. The sensor device according to claim 37, further comprising a data processor operably coupled to pulmonary airflow sensor, wherein the sensor device is capable of integrated collection of data obtained via the pulmonary airflow sensor and the non-spirometric cardiopulmonary activity sensor.

39. A method for collecting physiological data about a subject, comprising obtaining cardiopulmonary data about a subject via the sensor device of claim 38.

40. The method according to claim 39, wherein the method for collecting physiological data about a subject comprises a method for diagnosing a disease or physiological condition of the subject.

41. The method according to claim 40, wherein the sensor device further comprises a data transmitter operably coupled to the data processor, and the method further comprises transmitting the cardiopulmonary data obtained by the device to an external repository.

42. The method according to claim 39, wherein the subject is a human.

43. The sensor device according to claim 35, further comprising a data processor.

44. The sensor device according to claim 43, further comprising a temperature sensor operably coupled to the data processor, wherein the sensor device is capable of integrated collection of data obtained via the pulmonary airflow sensor and temperature sensor.

45. The sensor device according to claim 44, wherein the temperature sensor is capable of measuring the body temperature of a subject.

46. The sensor device according to claim 44, further comprising a data transmitter coupled to the data processor.

47. A method of making a sensor device for sensing cardiopulmonary activity, comprising:

providing an elongated housing having a proximal end defining a respiratory port, a distal end defining an airflow port positioned so as to cause air to flow in a longitudinal direction through the airflow port, and a lumen;

placing an airflow sensor inside the housing lumen and operably coupling the airflow sensor to a data processor; and coupling a non-spirometric cardiopulmonary activity sensor to the housing and operably coupling the non-spirometric cardiopulmonary activity sensor to the data processor, wherein the sensor device is capable of integrated collection of cardiopulmonary data obtained via the airflow sensor and the non-spirometric cardiopulmonary activity sensor.

48. The method according to claim 47, further comprising operably coupling a temperature sensor to the data processor, wherein the temperature sensor is capable of measuring body temperature, and wherein the sensor device is capable of integrated collection of cardiopulmonary data obtained via the airflow sensor, the non-spirometric cardiopulmonary activity sensor, and the temperature sensor.

49. A method of making a sensor device for sensing cardiopulmonary activity, comprising:

providing an elongated housing having a proximal end, a distal end, and a lumen;

placing an airflow sensor inside the housing lumen and operably coupling the airflow sensor to a data processor; and coupling a non-spirometric cardiopulmonary activity sensor to the housing and operably coupling the non-spirometric cardiopulmonary activity sensor to the data processor, wherein the sensor device is capable of integrated collection of cardiopulmonary data obtained via the airflow sensor and the non-spirometric cardiopulmonary activity sensor;

providing a first airflow tube displaced within the housing lumen, the first airflow tube having a first airflow tube diameter; and providing a second airflow tube displaced within the housing lumen, the second airflow tube having a second airflow tube diameter, wherein the first airflow tube diameter is less than the second airflow tube diameter.

50. A sensor device for obtaining cardiopulmonary data, comprising:

an elongated housing having a proximal end, a distal end, and a lumen, wherein the proximal housing end defines a respiratory port that is in fluid communication with the lumen;

an airflow port defined in the housing adjacent the distal end of the lumen, the airflow port being in fluid communication with the lumen;

an airflow sensor positioned within the lumen;

a microphone positioned within the lumen, the microphone being operable to detect a physiological sound of a subject; and a data processor operably coupled to both the airflow sensor and the non-spirometric cardiopulmonary activity sensor, wherein the sensor device is capable of integrated collection of cardiopulmonary data obtained via the airflow sensor and the non-spirometric cardiopulmonary activity sensor.

51. A method for collecting physiological data about a subject, comprising obtaining cardiopulmonary data about a subject via the sensor device of claim 50.

52. The method of claim 51, wherein obtaining cardiopulmonary data about a subject comprises detecting heart sounds of the subject via the sensor device.

53. The method of claim 51, wherein the method for collecting physiological data about a subject comprises:

detecting and recording a physiological sound of the subject using the sensor device; and listening to a recorded physiological sound to diagnose a disease or physiological condition of the subject.

* * * * *